United States Patent
Notton et al.

[11] Patent Number: 5,735,286
[45] Date of Patent: Apr. 7, 1998

[54] APPARATUS AND PROCESS FOR MEASURING AND PROCESSING PHYSIOLOGICAL SIGNALS

[76] Inventors: Philippe Notton, 7 Chemin des Dames, 57500 Saint-Avold; Daniel Schang, 9 rue George Sand, 57730 Folschviller, both of France

[21] Appl. No.: 586,920

[22] PCT Filed: Jul. 25, 1994

[86] PCT No.: PCT/FR94/00930

§ 371 Date: Mar. 20, 1996

§ 102(e) Date: Mar. 20, 1996

[87] PCT Pub. No.: WO95/02991

PCT Pub. Date: Feb. 2, 1995

[30] Foreign Application Priority Data

Jul. 23, 1993 [FR] France ................. 93 09262

[51] Int. Cl.$^6$ ........................................... A61B 5/02
[52] U.S. Cl. ...................... 128/700; 128/670; 128/672
[58] Field of Search ........................... 128/700, 668, 128/670, 672

[56] References Cited

U.S. PATENT DOCUMENTS

| 4,562,843 | 1/1986 | Djordjevich et al. | 128/672 |
| 5,025,784 | 6/1991 | Shao et al. | 128/700 |
| 5,584,298 | 12/1996 | Kabal | 128/677 |

*Primary Examiner*—Marvin M. Lateef
*Assistant Examiner*—George R. Evanisko
*Attorney, Agent, or Firm*—Notaro & Michalos PC

[57] ABSTRACT

An apparatus and process for measuring and processing physiological signals is portable, and have a device for capturing (3, 3'), shaping (4, 4') and digitizing (5) continuously at least one electrocardiographic signal and one signal representing the variation in impedance of a given volume (V) of the body (6) of a patient. A digital preprocessing unit (7) co-operating with control (8) and display (9) devices and a detachable memory (10) for the digitized signals or values token from significant parameters and, finally, by a central digital processing device (12) that collects and stores, by successive transfers, the data from the memory (10) and makes a comparison of them.

24 Claims, 7 Drawing Sheets

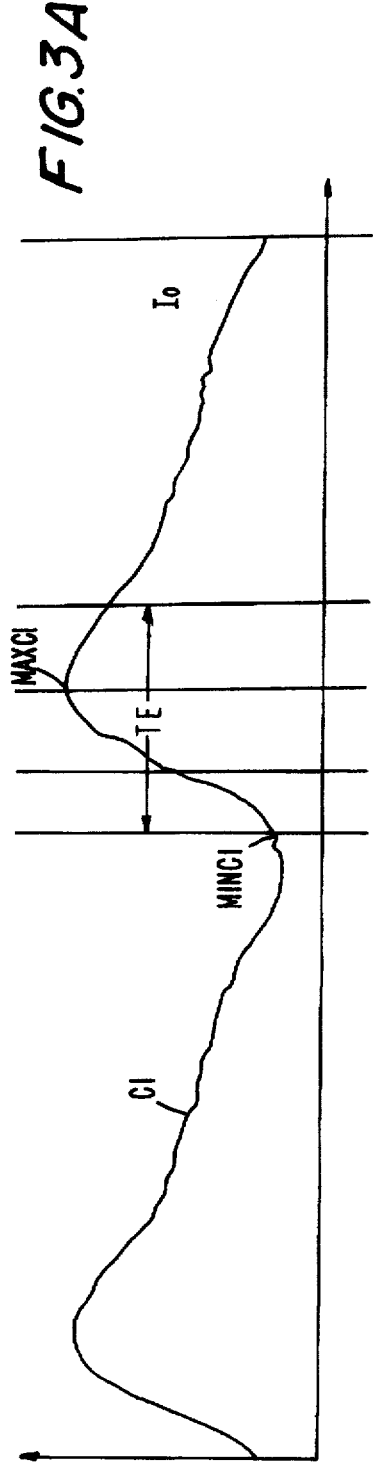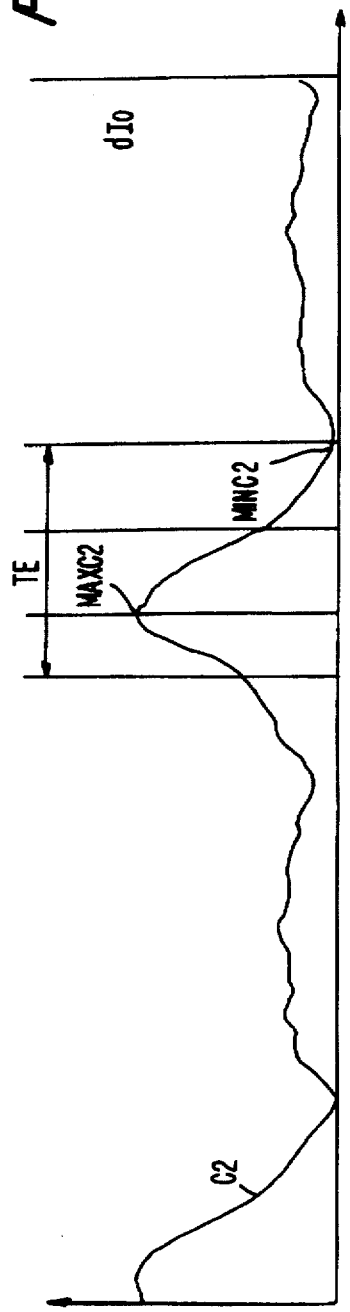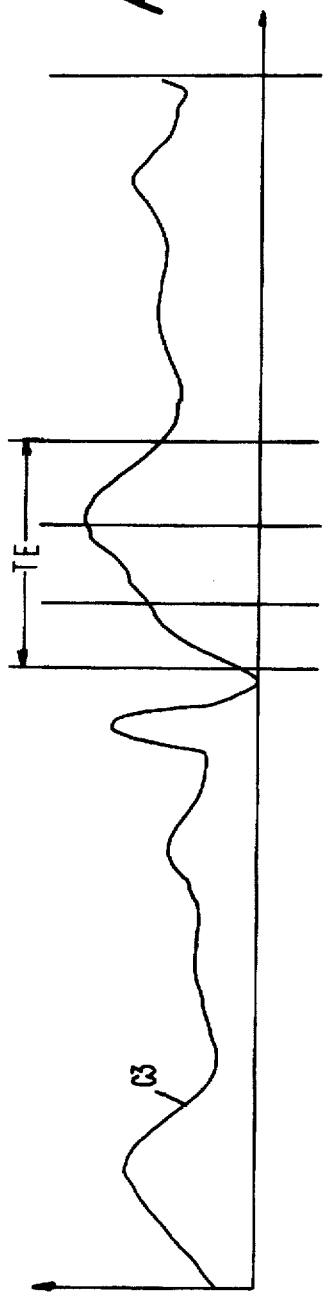

APPARATUS AND PROCESS FOR MEASURING AND PROCESSING PHYSIOLOGICAL SIGNALS

FIELD AND BACKGROUND OF THE INVENTION

The present invention concerns the field of medical examinations, particularly medical monitoring over long periods and diagnostic aid, and has as its subject-matter an apparatus for measuring and processing physiological signals and an automatic process used by said apparatus.

At present, cardiac output and blood pressure are measured by separate apparatuses and only at significant intervals of time and in special conditions, i.e. at medical consultations or examinations by specialists.

Furthermore, blood pressure is determined by mechanical devices, which require compression and are consequently not suitable for continuous use.

Similarly, cardiac output, which is generally measured by invasive methods, requires cumbersome equipment and cannot be determined continuously over a long period.

There are also various types of apparatus using the principles of the variation in impedance of a given volume of the human body, allowing the cardiac output to be measured non-invasively.

However, these types of apparatus are fixed and non-portable and therefore do not allow the cardiac output of a patient in everyday life to be determined continuously.

Furthermore, they require analogue processing or, at least, preprocessing, of the signals recorded, which is subject to much interference, and the calculation formulae used do not rest absolutely on anatomical or physiological criteria.

Moreover, these known types of apparatus do not permit the simultaneous determination of blood pressure (mean, systolic or diastolic) and do not record the signals taken and/or the parameters calculated over long periods, with a view to subsequent global use. Finally, these types of apparatus mentioned above do not permit the capture and recording, separately and simultaneously, of at least one electrocardiogram signal, which allows the source and nature of the informative signals for processing to be diversified.

SUMMARY OF THE INVENTION

The present invention is aimed particularly at remedying all the above disadvantages. To this end, it has as its subject-matter an apparatus for measuring and processing physiological signals for the determination of cardiac and circulatory parameters, characterised in that it is constituted principally, on the one hand, by means for capturing, shaping and digitising continuously at least one electrocardiographic signal and one signal representing the variation in impedance of a given volume of the body of a patient, said means being connected to electrodes arranged at specific locations on the latter and, on the other hand, by a digital preprocessing unit co-operating with control and display means and a detachable storage means and/or a means for transmitting all the digitised signals or values taken from significant parameters, for each heartbeat, on the basis of said digitised signals and, finally, by a central digital processing device that collects and stores, by successive transfers, the data from the storage means or the transmission means and that permits the analysis of said data or said parameters over long time periods, their comparison with previous data or parameter values and the display and/or printing out of all the data being capable of serving for the preparation of a diagnosis.

The invention also has as its subject-matter an automatic measurement and processing process used by the apparatus described above, characterised in that it consists in recording continuously, by means of electrodes, at least one electrocardiographic signal and one signal representing the variation in impedance of a given volume of the body of a patient, delimited by transmitting electrodes and receiving electrodes, in filtering and digitising these signals, then in processing them by calculating the corresponding derivative signals and by determining the values, for each heartbeat, of various cardiac and circulatory parameters, in displaying in real time, as chosen by the user or the patient, the value or values of one or more of said parameters, in storing continuously, for a defined period, all the aforementioned digital signals and also the successive values of said parameters on a detachable and transportable medium and, finally, in transferring and manipulating the data stored on said media, particularly with a view to analysing them as a whole, comparing them with data collected previously and printing them out in graph or table form.

BRIEF DESCRIPTION OF THE DRAWINGS

It will be easier to understand the invention from the following description, which relates to a preferred embodiment, given by way of non-exhaustive example, and explained with reference to the attached diagrammatic drawings, in which:

FIGS. 3A, 3B and 3C represent respectively, in the form of timing diagrams, the signal corresponding to the variation in impedance of a defined volume of the body of a patient, the derivative of the preceding signal and the derivative of the electrocardiographic signal;

DESCRIPTION OF THE PREFERRED EMBODIMENT

Figure 1:
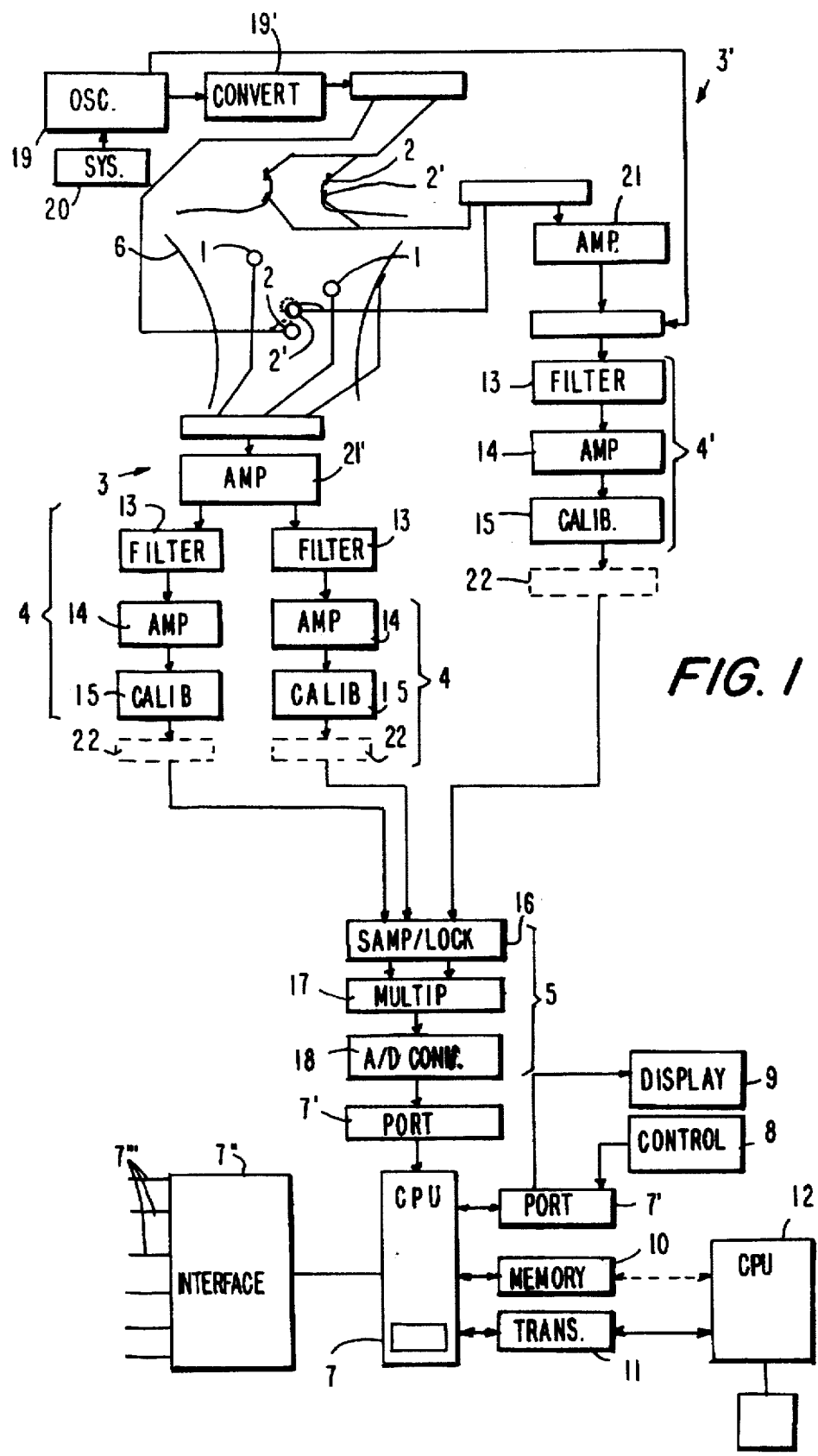
FIG. 1 is a block diagram of the portable part of the apparatus in accordance with the invention, also showing the placing of the electrodes on a patient.
Figure 2:
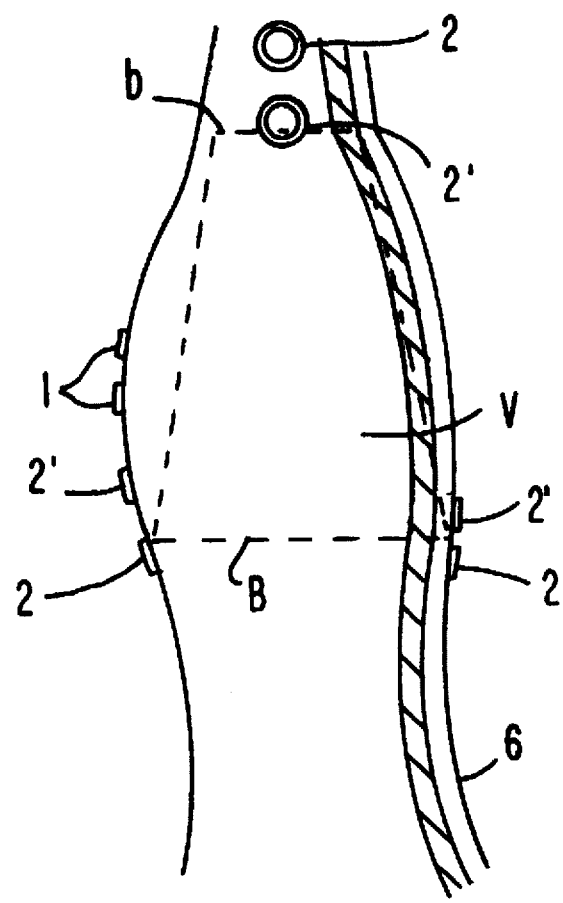
FIG. 2 is a side view of the portion of the patient's body shown in FIG. 1.

In accordance with the invention, and as shown in FIGS. 1 and 2 of the attached drawings, the measuring and processing apparatus is constituted principally, on the one hand, by means for capturing 3, 3', shaping 4, 4' and digitizing 5 continuously at least one electrocardiographic signal and one signal representing the variation in impedance of a given volume V of the body 6 of a patient, said means being connected to electrodes 1, 2, 2' arranged at specific locations on the latter and, on the other hand, by a digital preprocessing unit 7 co-operating with control 8 and display 9 means and a detachable storage means 10 and/or a means 11 for transmitting all the digitized signals or values taken from significant parameters FC, QC, WC, RV, IC, FE, PAM, PAS and PAD, for each heartbeat, on the basis of said digitized signals and, finally, by a central digital processing device 12 that collects and stores, by successive transfers, the data from the storage means 10 or the transmission means 11 and that permits the analysis of said data or said parameters over long time periods, their comparison with previous data or parameter values and the display and/or printing out of all The data being capable of serving for the preparation of a diagnosis.

According to a first embodiment of the invention, the capturing, shaping and digitizing means 3, 3', 4, 4' and 5, and the preprocessing unit 7 are produced by means of integrated circuits and grouped, together with the control and display means 8 and 9, in a compact portable housing, which may be dust and damp-proof, provided with its own power supply, the detachable storage means 10 consisting of a very high-capacity plug-in memory card.

By giving a measuring apparatus to each patient, this arrangement makes it possible to record and exploit, on a continuous basis, the electrocardiographic signal or signals and the impedance variation signal of a patient, who can move about freely, in the context of his life and everyday activities.

This means that the use of this apparatus is not accompanied by any unpleasant constraints on the patient (no compression, no limitation of everyday movements) and does not present any risk in use (in particular, measurement by non-invasive technique).

Furthermore, the various parameters calculated FC, QC, WC, FE, PAM, PAD and PAS can be displayed in real time, for example by means of a liquid crystal screen 9, as chosen by the patient carrying said housing or by another person, transmitted to the digital preprocessing unit 7 via a touch-sensitive keyboard 8, for example. The latter can also be used to initialise said digital preprocessing unit 7, particularly by taking into consideration various parameters specific to each patient.

Since the autonomy of the portable housing is limited mainly by the memory capacity of the storage means 10, it is advantageous to choose a memory card of a flash-type, complying with the standard known by the title PCM CIA which, after a data compression operation, allows the digitized signals, the signals obtained after processing, and the parameters calculated for each heartbeat, to be stored, for a period of at least twenty-four hours.

In accordance with a second advantageous embodiment of the apparatus according to the invention, not shown in the attached drawings, the capturing, shaping and digitizing means 3, 3', 4, 4' and 5, in the form of integrated circuits, are arranged in a first housing connected to the electrodes 1, 2, 2', and the preprocessing unit 7 and the control and display means 8 and 9 are grouped together in a second housing, which may be attached to the wrist of the patient, the connection between the two aforementioned housings being of the wire type or by electromagnetic waves.

Nevertheless, said housing could also be implemented in a fixed version independent of or integrated into another medical monitoring apparatus, particularly for clinical applications, for example, in which case it then has a direct main supply and is connected to the central device 12 by means of a specialized link of the RS232 type or a conventional serial link for the continuous transfer of the digitized signals and, if appropriate, the values of the parameters calculated for each heartbeat.

According to another characteristic of the invention, shown in FIG. 1 of the attached drawings, the signal representing the variation in impedance is captured by means of a synchronous detection device 3' causing an adjustable high frequency (40 kHz–120 kHz), low-intensity (1 mA) electric current to flow through a defined volume V, of a tapered shape, of the trunk of a patient and between a set of transmitting electrodes 2 and a set of receiving electrodes 2', the locations of which delimit said volume V.

Said synchronous detection device 3', the principle of which is known to the person skilled in the art, uses an oscillator circuit 19 (very low-distortion sine) provided with an ancillary system 20 (stabilisation+adjustment of the oscillator frequency 19) to produce a high-frequency signal generally of around 75 kHz which, when converted by a suitable circuit 19' into a low-intensity current signal (of the order of 1 mA), is applied at transmitting electrodes 2, then collected, after transmission through the body 6 of the patient, by receiving electrodes 2'. The signals collected by the latter are then applied to a differential amplifier 21 (with a very high input impedance), the output signal of which is exploited, using the high-frequency signal produced by the oscillator 19, with a view to extracting the signal representing the variation in impedance of the volume V defined by the electrodes 2 and 2'.

The means 3 for capturing the electrocardiographic signal can consist of a simple differential amplifier 21'.

The means 4 for shaping the electrographic signal at least which has been recorded and the means 4' for shaping an impedance variation signal are similar in structure and are constituted by highly selective filtering modules 13 (48 Hz/10th order analogue filtering) to stabilize the curves recorded, by modules 14 for amplifying and modules 15 for calibrating the signals recorded.

The means 5 for digitizing the shaped signals advantageously comprise a sampling/locking device 16, the output of which is connected via a multiplex circuit 17, to an analogue-to-digital conversion circuit 18, preferably on 12 or 16 bits.

Finally, the digital preprocessing device 7 preferably consists of a 12- or 16-bit microprocessor provided with various input/output ports 7' and a ROM-type memory containing the various programs for managing the various means 3, 3', 4', 5, 8 and 9, for determining the values of the parameters and for storing the data after compression.

According to another characteristic of the invention, the transmission and measurement frequency of the synchronous detection device 3' can be adjusted digitally to an optimal value for a given patient and the gains of the signal amplification means 14, 21 forming part of the means 4' for shaping the impedance variation signal and/or the synchronous detection device 3' can also be adjusted digitally, for example by the central device during an initialisation phase.

As shown in FIG. 1 of the attached drawings, the measurement device according to the invention can also comprise an interface module 7", provided with sampling and analogue-to-digital conversion circuits, so that several signals supplied by additional sensors attached to the patient can be provided in digital form to the processing unit 7 via several connection or data entry lines 7'".

It is therefore possible to digitize and record simultaneously several other signals giving information on the condition of the patient and, immediately or later, to compare in real time and without any phase-shift the ECG signal, the impedance variation signal, and the various signals supplied by the related sensors.

The analog signals recorded by the aforementioned related sensors could for example consist of: aortic pressure signal, carotidogram, piezoelectric signal, first derivative signal of the left ventricular segmentary kinetics or similar, the synchronous display of all these signals, in addition to those specifically recorded by the apparatus transforms the latter into a true portable polygraph.

FIGS. 1 and 2 illustrate a first embodiment of the invention using four pairs of transmitting/receiving electrodes 2, 2' for measuring the variation in impedance of a volume V of a patient's body, two pairs of electrodes 2, 2' being arranged near the neck and the other two pairs being arranged above the waist.

According to a second embodiment of the invention, the apparatus will advantageously comprise only two transmitting electrodes 2 and two receiving electrodes 2', a first pair of transmitting/receiving electrodes 2, 2' being intended to be applied to the skin of the patient in the area of the upper portion of the manubrium sterni, the other pair of electrodes 2, 2', combined with or in addition to said first pair, being intended to be applied in the area of the xiphoid process.

Figure 5:
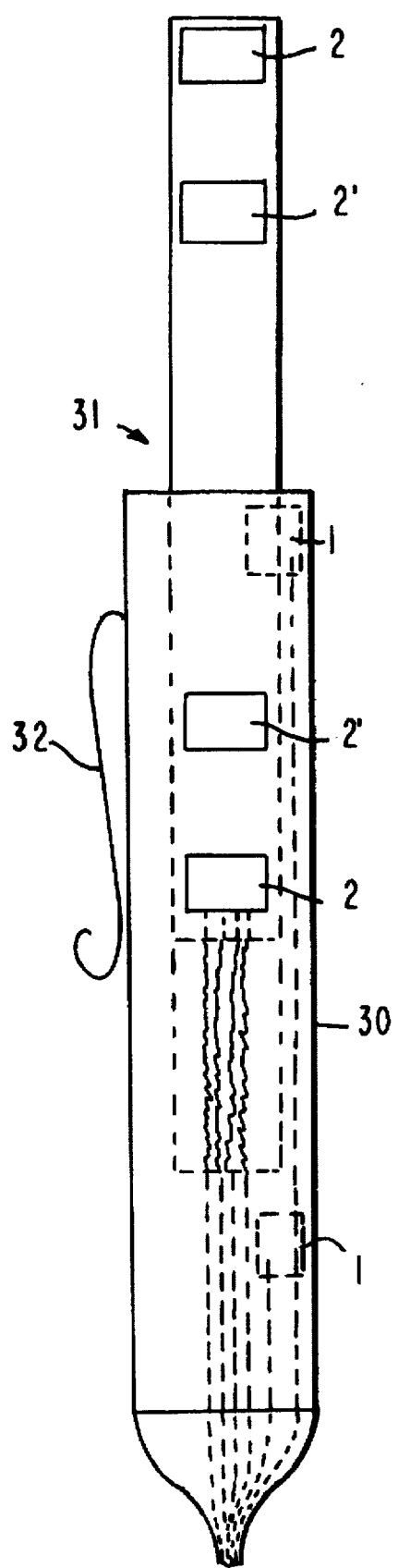
FIG. 5 is a side view of electrode supports forming part of an apparatus according the invention.

In accordance with a characteristic of the invention, shown in FIG. 5 of the attached drawings, the two pairs of electrodes 2, 2' are mounted respectively on a main support 30 and on a secondary support 31, which are elongated in form and can slide relative to one another so as to move the two pairs of electrodes 2, 2' farther apart from or closer to each other, it being possible to determine visually the distance between the two receiving electrodes 2' by means of a graduation.

The main support 30 can with advantage take the form of a tube and, in addition to a pair of electrodes 2, 2', can have two electrodes 1 for capturing the electrocardiogram and a hooking means 32 and the secondary, support 31 can take the form of a small ruler or a graduated tongue, that can be slid telescopically relative to the main support 30 and carries a pair of electrodes 2, 2' at its free end, transmission between said electrodes 1, 2 and 2' and the capture means 3, 3' being possible by wire or by infrared waves.

The electrodes 1, 2 and 2' can consist of square portions of a noble metal, measuring about 1 cm², crimped to the supports 30 and 31, the receiving electrodes 2' being located between the two transmitting electrodes 2 and about 5 cm from the latter.

The main support 30/secondary support 31 assembly thus forms a compact device that can be transported like a large pen in the retracted position, and manipulated by telescopically extending the "ruler" 31 and applying the electrodes 1, 2, 2' to the patient's skin.

As also shown in FIG. 1 of the attached drawings, an optical insulation device 22 can be arranged between the means for capturing 3, 3' and shaping 4, 4' the signals, on the one hand, and the means for digitizing 5 the signals, on the other hand, so that the patient's maximum safety is ensured however the apparatus according to the invention is used.

However, in its portable version, since the power supply to the apparatus in accordance with the invention is generally by batteries or by a rechargeable battery, such an optical insulation device 22 is generally unnecessary.

The practical production of the various devices, modules or electronic circuits described above is known to the person skilled in the art and therefore does not require more detailed description.

It should however be noted that the various digital signals are encoded on at least 12 bits, which makes it possible to obtain high dynamics.

The invention also has as its subject-matter an automatic measurement and processing process used by the apparatus described above consisting, after various initialisation operations in recording continuously, by means of electrodes 1, 2, 2', at least one electrocardiographic signal and one signal representing the variation in impedance of a given volume V of the body 6 of a patient delimited by transmitting electrodes 2 and receiving electrodes 2' in filtering and digitizing these signals, then in processing them by calculating the corresponding derivative signals and by calculating the values, for each heartbeat, of various cardiac and circulatory parameters FC, QC, WC, RV, IC, FE, PAM, PAD, PAS, in displaying in real time, as chosen by the user or the patient, the value or values of one or more of said parameters, in storing continuously for a defined period, all the aforementioned digital signals and also the successive values of said parameters on a detachable and transportable medium 10 or in a high-capacity memory and, finally, in transferring and manipulating the data stored on said medium 10 or in said memory, particularly with a view to analysing them as a whole, comparing them with data collected previously and printing them out in graph or table form.

According to a characteristic of the invention, the operations of capture, filtering, digitization, processing, display and storage on a detachable medium 10 are performed by using means 3, 3', 4, 4', 5, 7 and 9 grouped together in a portable housing with its own power supply, provided with electrodes 1, 2 and 2' in order to record the signals to be processed and stored.

The cardiac output QC is determined by exploiting, through digital processing, various characteristics of the curves C1, C2 and C3 and by defining, together with anatomical criteria, the volume V for which the variation in impedance is being recorded.

To make it possible to obtain information permitting an effective diagnosis of the patient concerned, the process according to the invention consists in determining particularly, for each heartbeat, using the curves C1, C2, C3 corresponding respectively to the signal I representing the variation in impedance of a defined volume V of the body 6 of a patient, to the time derivative dI/dt of the preceding signal, and to the time derivative of the electrocardiographic signal, the heart rate FC, the cardiac output QC, the cardiac work WC and the mean PAM, systolic PAS and diastolic PAD blood pressures.

As can be seen in FIG. 2 of the attached drawings, the volume V delimited by the electrodes 2, 2' consists of a truncated cone, the small base b of which is located near the neck of the patient and the large base B of which is located near the waist of the patient, making it possible to define a constant K such that:

$$K = H \times (D^2 + d^2 + D \times d - 3250)/60$$

with

H=height of the truncated cone in cm,

D=diameter of the large base in cm, d=diameter of the small base in cm.

However, by using two pairs of electrodes 2, 2' mounted on supports 30 and 31, the volume V used for measuring the variation in impedance consists of a truncated cone located between the neck and the thorax at the scyphoid level, allowing a constant K to be defined such that:

$$K = H \times (C^2 + C^2 + Cc - 2250)/60$$

with

H=distance between the two receiving electrodes 2',

C=circumference of the thorax at the scyphoid level,

C=circumference of the neck

This constant K is determined for each patient and its value is communicated to the digital preprocessing unit 7 during the initialisation operations.

In accordance with the invention, the process consists first in calculating, for each heartbeat, the value of the ratio IC=dIo/Io, where Io represents the difference between the maximum value MAXC1 and the minimum value minC1 of the curve C1, and dIo represents the difference between the maximum value MAXC2 and the most frequent value of the curve C2, this being for each heartbeat (FIGS. 3A and 3B), the two curves C1 and C2 having identical scales of ordinates.

Then, taking account of the value of IC calculated, as indicated above, for each heartbeat, and of the value of the constant K programmed before the start of the process, the process according to the invention consists in determining the systolic ejected volume VES in liters and the heart output QC in liters/minute by the following formulae:

$$VES = K \times IC \times TEV$$

and $$QC = VES \times FC.$$

where TEV, the ventricular ejection time in s, is given by the formula:

$$TEV = H \times [(MINC2 - MAXC1) - (MAXC1 - MAXC2)],$$

with H=1.5±0.15, MINC2 being the minimum value of the curve C2 for the heartbeat in question.

The heart rate FC expressed in beats/minute is preferably taken from the derivative of the electrocardiographic signal, and therefore from the curve C3, and thus makes it possible to be free from the interference that often affects the electrocardiographic signal (FIG. 3 C).

The momentary heart rate FC (in beats per minute) can be calculated by using the following formula:

$$FC = (1000/ROR1) \times 60$$

where ROR1 represents the time difference in milliseconds between two consecutive complexes, it being possible to measure this difference directly on the curve C3 of FIG. 3.

Figure 4:
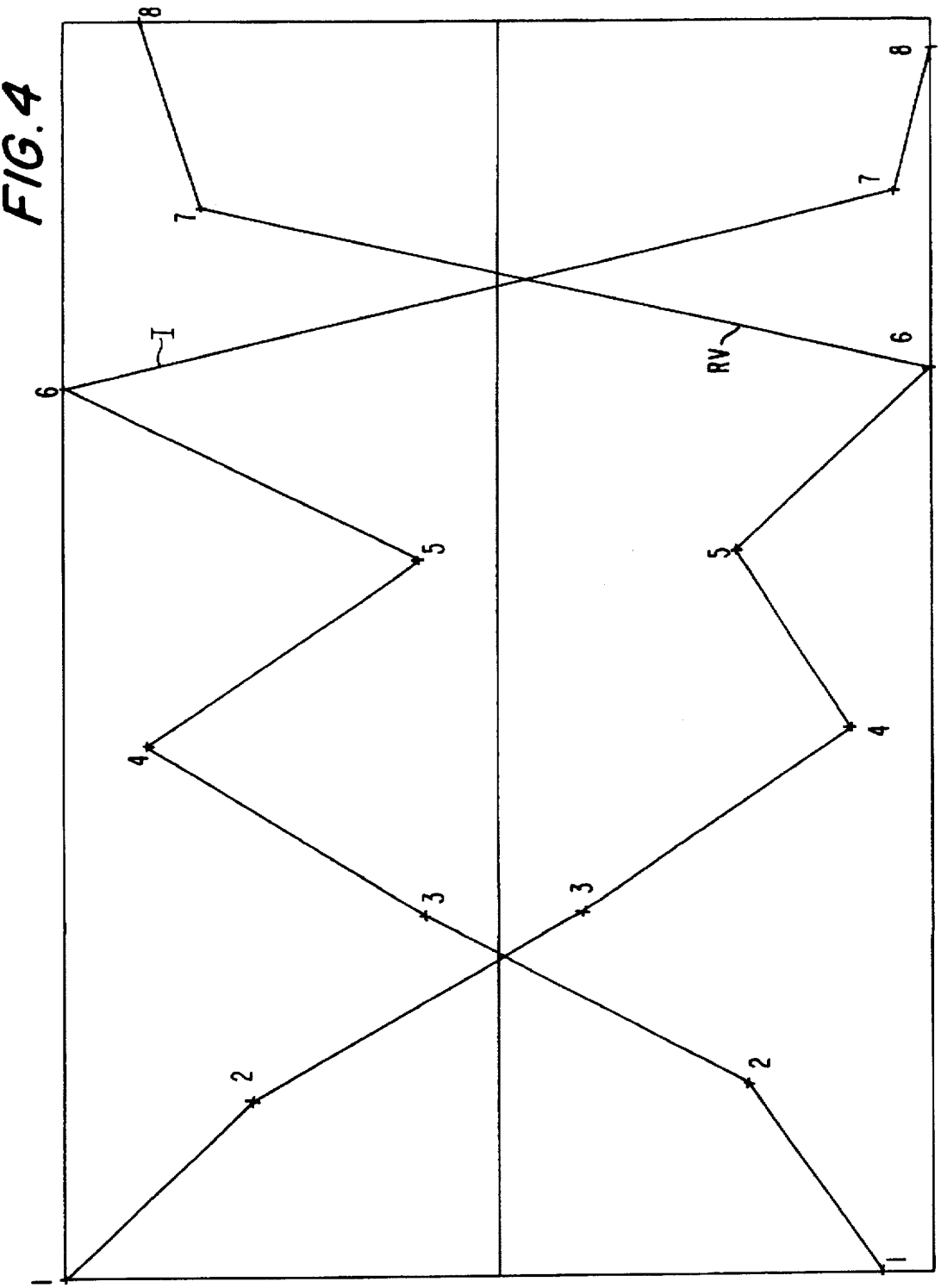
FIG. 4 shows, for different successive heartbeats, the curves for the evolution in indexed peripheral resistance RV and the ratio IC.

During the various series of trials the surprising fact was noted that the curve representing the evolution of the ratio IC and the curve representing the evolution of the indexed peripheral resistance RV had structures that were symmetrical relative to an axis, the values of IC and RV for each heartbeat shown on the same graph, being arranged on either side of a median axis (FIG. 4).

The present invention makes advantageous use of this surprising feature with a view to determining the mean blood pressure PAM.

To this end, the process according to the invention consists, on the basis of the ratio IC calculated for each heartbeat, in determining the indexed peripheral resistance RV in dynes/cm$^5$/m$^2$ using the following formula:

$$RV = \frac{(RV2 - RV1)(IC - IC1)}{IC2 - IC1}$$

where RV1 and RV2 represent values of RV, and IC1 and IC2 represent values of IC, all determined manually for two different states of the patient (at rest and when exerting effort) and stored during the initialisation operations.

By preference, several values for RV and IC will be recorded and stored prior to implementing the process according to the invention, the values RV1, RV2, IC1 and IC2 chosen, if appropriate, automatically during the initialisation operations, being those that best verify the aforementioned role of symmetry.

The mean blood pressure PAM can then be calculated, for each heartbeat, by using the following formula:

$$PAM = \frac{RV \times QC}{80 \times SC}$$

where QC represents the cardiac output, RV the indexed peripheral resistance and SC the body surface of the patient undergoing the process, the value of cardiac work WC then being determined by the formula:

$$WC = \frac{0.0144 \times PAM \times QC}{SC}$$

The value for the body surface SC in cm$^2$, given by the formula [Height (in cm)+Weight (in kg)−60]/100, will also be stored, for each patient, as a constant.

In accordance with another characteristic of the invention, the diastolic blood pressure PAD can then be determined, for each heartbeat, by means of a polynominal function such that:

$$PAD = F(X, Y)$$

with $$X = A(RV - B)$$

and $$Y = C \times (WC - D)$$

where A, B, C and D represent constants, the polynominal function F (X, Y) preferably having a formulation of the type:

$$F(X, Y) = G \times (X+Y) - I \times (X+Y)^2 - J \times (X \times Y) + K + L,$$

where G, I, J, K and L represent constants.

The values of the constants A, B, C, D, G, I, J, K and L can be calculated by performing a large number of successive examinations during which values of RV, PAD and WC will be determined separately.

Nevertheless, for the purposes of information, these various constants could have the following values:

A=0.0035, B=2150, C=1.8, D=4.5, G=6.4, I=41, J=165, K=2140 and L=128.

On the basis of the values of PAM and PAD, it is then easy to determine the value of PAS, since it is known that:

$$PAM = \frac{1}{3} PAS + \frac{2}{3} PAD.$$

According to another characteristic of the invention, it is also possible To determine by calculation the ejection fraction FE by using the formula:

$$FE = -3.54 \times W + 60$$

on the basis of the parameters:

$$D = \sqrt{1/2 \times A^2 + 1/2 \times B^2 - AB}$$

where:

A=(RV−2150)/450 and
B=(WC−4.5)/0.9
with:
W=D if A−B≧0
and
W=−D if A−B≦0.

Figure 6:
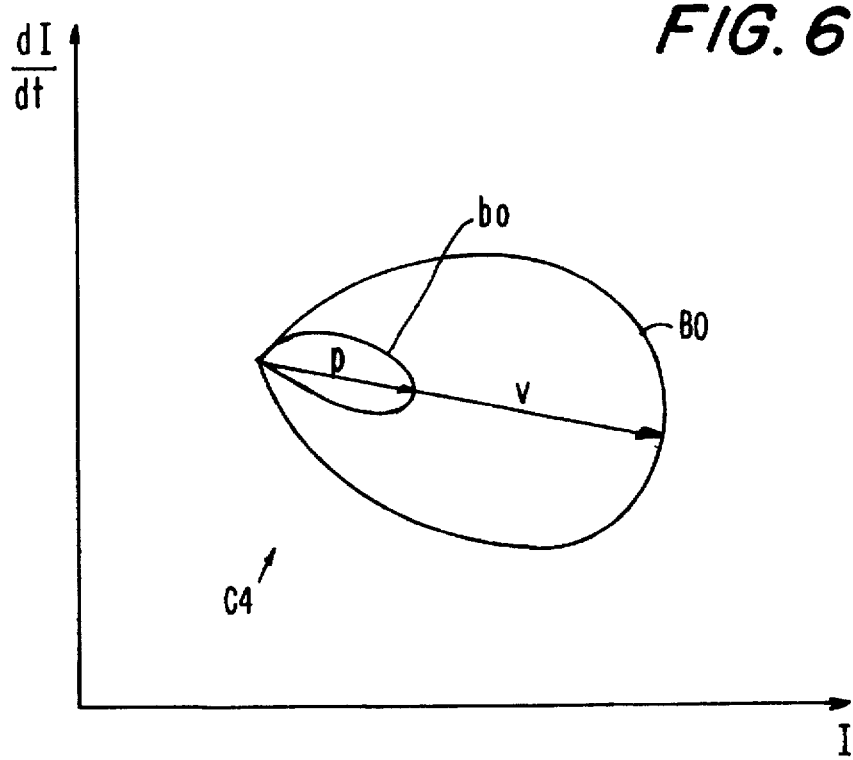
FIG. 6 shows the curve C4: $dI/dt = F'(I)$ established in accordance with the process according to the invention.

As shown in particular by FIG. 6 of the attached drawings, the process according to the invention can also consist in establishing digitally, for each heartbeat, a curve C4 expressing the function dI/dt=F'(I) and constituted by a first ovoid loop BO representing the mechanical systole and by a second ovoid loop bO representing the diastole, then in calculating the ratio between the lengths of the major axes of the two loops BO and bO with a view to subsequent calculations of pressure/volume if necessary.

Indeed, the dimensional ratio of the axis BO/axis bO is, in the opinion of the inventors, correlated with the telediastolic auricular ejected volume/telediastolic ventricular volume and consequently represents an index that is close to the left ventricular compliance.

Figure 7:
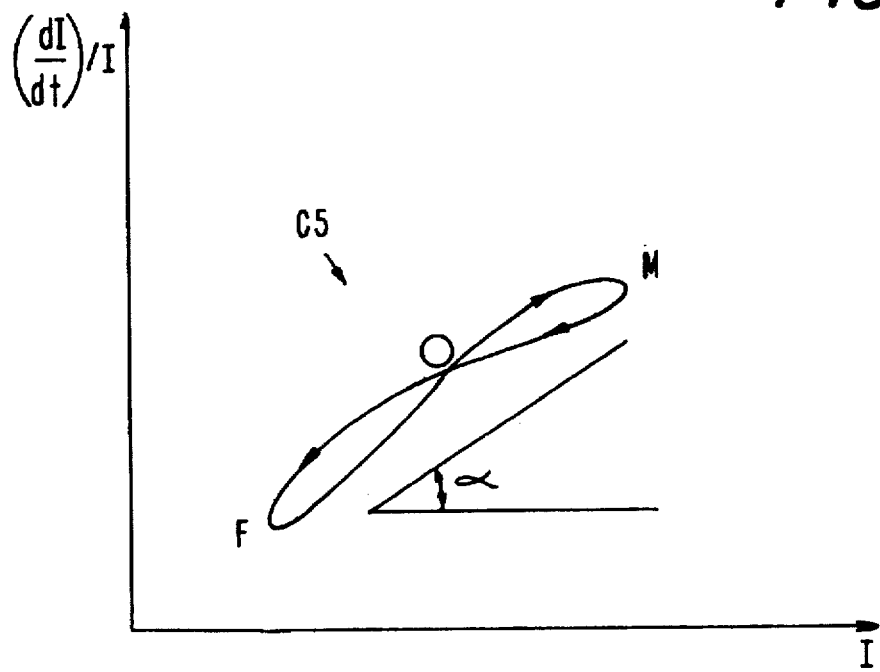
FIG. 7 shows the curve C5: $(dI/dt)/I = F''(I)$ established in accordance with the invention.
Figure 8:
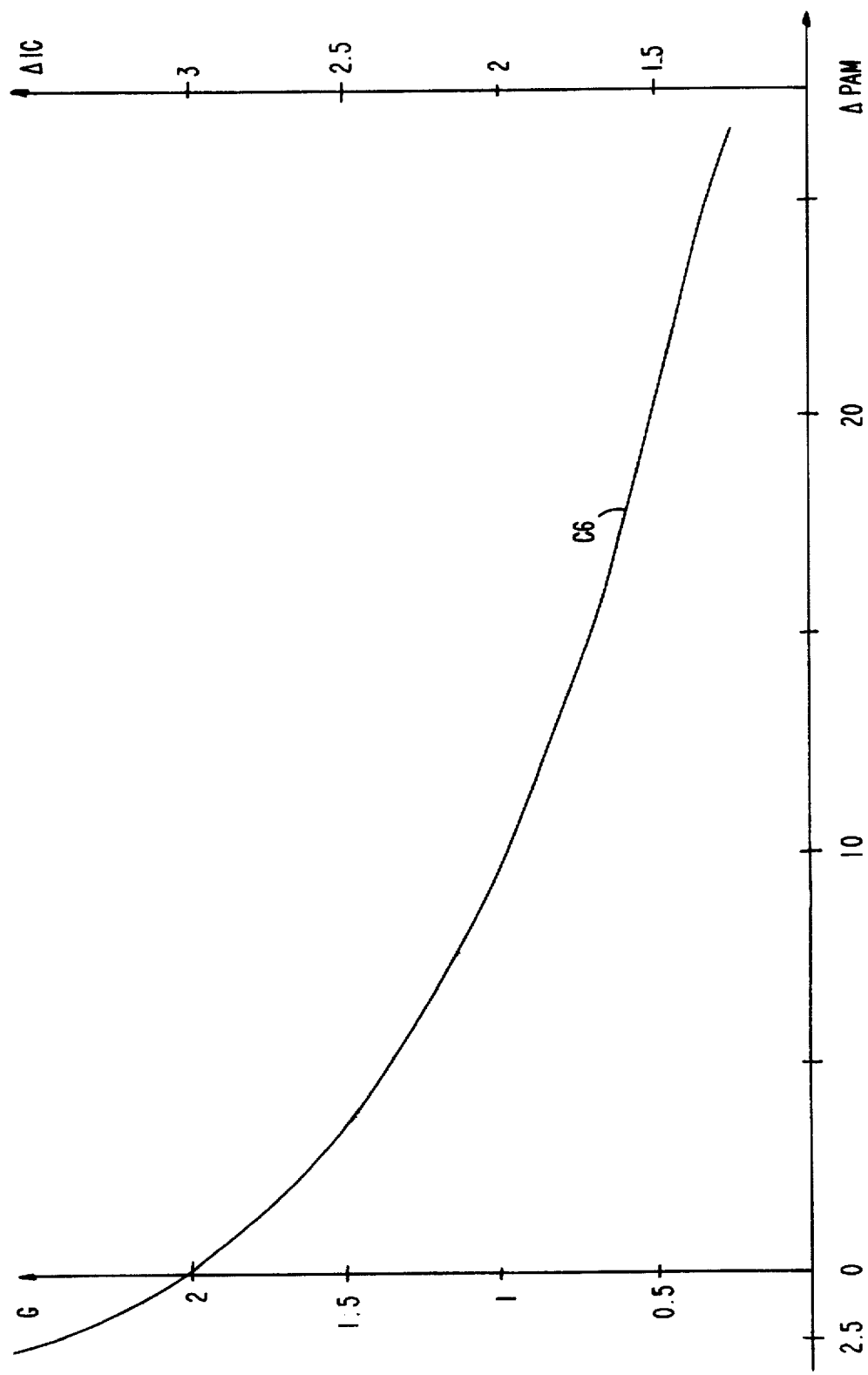
FIG. 8 represents the experimental regression curve C6 established according to the invention.

According to a embodiment of the invention, illustrated by FIG. 7 of the attached drawings, the process can also consist in establishing digitally, for each heartbeat and on the basis of numerical values determined for the curves C1 and C2, a curve C5 expressing the function (dI/dt)/I=F''(I), where I represents the successive recorded values of the impedance of a defined volume V of the body of the patient during a cardiac cycle, and taking the form of a flattened figure of eight, the longitudinal axis of which is inclined by an angle α relative to the axis corresponding to the variable I, then in measuring or calculating the time taken to pass from the point O of intersection of the curve C4 to the point F located at the distal end of the lower loop of said curve C4, this time corresponding to the ventricular ejection time TEV.

In accordance with variant embodiment of the invention, the process can consist in calculating a coefficient:

$$G = (10^4 \times PFr \times 1.8)/(PAMr \times RVr \times Sc)$$

where PFr, PAMr and RVr represent respectively the values of the ratio VES/TEV, of the mean blood pressure and of the indexed peripheral resistance, measured on a patient in the rest state and SC the body surface, then in determining by means of a regression curve C6, prepared beforehand using a large number of experiments and measurements on different patients, the incremental values ΔPAM and ΔIC which, using values for PAM and IC measured or calculated for the patient in question at rest, make it possible to calculate the maximum values PAM max and IC max of PAM and IC by adding the incremental values ΔPAM and ΔIC to the respective values at rest PAMr and ICr, with IC max=ICr×(1+G/10), then in calculating RV at Nc max by using the formula:

$$PAM\ max = (QC\ max \times RV\ at\ Nc\ max)/(80 \times SC)$$

where QC max represents the maximum cardiac output and Nc max represents the maximum heart rate (in beats/minute) and, finally, in determining said curves RV and IC for the patient in question by using the property of axial symmetry of the curves representing RV and IC, and in calculating the maximum values of the diastolic blood pressure PAD and the systolic blood pressure PAS.

The arrangement described above makes it possible to avoid, during the initialization phase, making a measurement of the parameters RV and IC in particular, for a state of effort in the patient, and allows said process to be used by patients who are at risk, confined to bed, etc.

Thus it is possible, through a single measurement made in the rest state (preferably the mean of measurements taken for the standing position and recumbent position) to determine the blood pressure, the output, the ejection fraction and the ventricular work at the theoretical maximum physical capabilities of an individual or patient, which may be of great interest for selecting or training sportsmen or women.

Consequently it is also possible to assess the reserves of a patient with cardiac insufficiency, hypertension or arrhythmia before anaesthesia, before or after therapy, before or after a surgical operation or the like.

With a view to optimising the capture of the impedance variation signal while avoiding interference as far as possible, the process can also consist in transmitting, during the initialisation operations, test signals at the transmitting electrodes 2, in order to determine, in particular, by frequency scanning, the transmission frequency that gives the clearest signal on reception at the receiving electrodes 2'.

Advantageously, the transmission frequency for measurements of variations in impedance is adjusted digitally, as a function of a comparative analysis of the signals recovered at the receiving antennae 2' for various transmission signals of different frequencies.

Furthermore, attempting to take into consideration only valid signals, the process according to the invention consists, after processing, in checking the digitised signals and the values of the parameters determined for each heartbeat, and in eliminating the signals and parameters with values outside a predetermined range, fixed during the initialisation operations.

By way of example, for twelve successive values calculated for the aforementioned parameters, those situated ±50% from the mean of said twelve values, then those situated ±30% from said mean will be eliminated in succession.

Finally, with a view to increasing the validity and reliability of the apparatus and making it easy to read the results of the measurements, said apparatus can with advantage calculate and display the values of the parameters FC, QC, WC, RV, IC, FE, PAM, PAS and PAD by establishing mean values over ten consecutive heartbeats.

Thus, the apparatus and the process in accordance with the invention make it possible to indicate the blood pressure of a patient at any time, continuously and in real time, in synchronism with the ECG signal, a haemodynamism signal and various signals from additional sensors.

Naturally, the invention is not limited to the embodiments described and illustrated in the attached drawings. Modifications are still possible, especially from the point of view of constituting technical equivalents, without thereby leaving the scope of protection of the invention.

We claim:

1. An apparatus for measuring and processing physiological signals to determine cardiac and circulatory parameters of a subject having a body with a surface, the apparatus comprising:

a plurality of electrodes (1,2,1',2') adapted to be connected to the surface of the body and distributed over the surface to delimit a volume in the body;

capturing means (3) connected to the electrodes for capturing at least one electrocardiographic signal from the subject and at least one impedance signal representing a variation in impedance of the volume of the body;

shaping means (4) connected to the capturing means for shaping the electrocardiographic and impedance signals;

digitizing means (5) connected to the shaping means for digitizing the shaped signals;

a digital preprocessing unit (7) having a control (8) for controlling operations of the unit and a display (9) for displaying results of the operations of the unit and, said digital preprocessing unit being connected to said digitizing means for receiving the digitized and shaped electrocardiographic and impedance signals;

said digital preprocessing unit (7) being programmed to calculate from the electrocardiographic and impedance signals, a plurality of significant parameter data for each heartbeat of the subject, the significant parameter data comprising heart rate (FC), cardiac output (QC), cardiac work (WC), peripheral resistance (RV), a ratio between a derivative of the electrocardiographic signal and a derivative of the impedance signal (IC), an ejection fraction (FE), mean blood pressure (PAM), systolic blood pressure (PAS) and diastolic blood pressure (PAD);

a central digital processing device (12) for collecting and storing the significant parameter data; and transfer means (10,11) connected between the digital preprocessing unit (7) and the central digital processing device (12) for transferring data from the unit (7) to the device (12), the transfer means comprising at least one of a detachable storage memory (10) detachably connected to the unit and the device for transferring data from the unit to the device, and a transmitting element (11) connected between the unit and the device for directly transferring data from the unit to the device;

said central digital processing device (12) being programmed for analyzing the significant parameter data over a period of a multiplicity of heartbeats, the analysis including comparing significant parameter data currently accumulated with previously accumulated significant parameter data, displaying data and printing data.

2. An apparatus according to claim 1, wherein the capturing, shaping and digitizing means (3, 3', 4, 4' and 5) and the preprocessing unit (7) comprise one set of integrated circuits with the control and display means (8 and 9), in a compact portable housing, with its own power supply, the detachable storage means (10) consisting of a very high capacity plug-in memory card.

3. A device according to claim 1, characterised in that the capturing, shaping and digitising means (3, 3', 4, 4' and 5), in the form of integrated circuits, are arranged in a first housing connected to the electrodes (1, 2, 2') and in that the preprocessing unit (7) and the control and display means (8 and 9) are grouped together in a second housing, which may be attached to the wrist of the patient, the connection between the two aforementioned housings being of the wire type or by electromagnetic waves.

4. An apparatus according to claim 1 wherein the capturing, shaping and digitizing means comprise respective integrated circuits, a first housing connected to said electrodes and containing said integrated circuits, a second housing, said pre-processing unit, said control and said display means being contained in said second housing, means for attaching said second housing to a wrist of a subject and connection means between said first and second housings which are selected from the group consisting of wires and contact-free electromagnetic waves.

5. An apparatus according to claim 4 wherein the volume of the body of the subject comprises a tapered volume within a trunk of the subject which is delimited by said electrodes, the apparatus including a synchronous detection device (3') connected to the electrodes for establishing an adjustable high-frequency low-intensity electric current flow through the trunk of the patient.

6. An apparatus according to claim 5 including an amplifier connected to the shaping means for shaping the impedance variation signal.

7. An apparatus according to claim 5 including an interface module (7") containing sampling and analog-to-digital conversion means, said interface module being connected to said pre-processing unit (7) for connecting additional sensors from the subject to the preprocessing unit.

8. An apparatus according to claim 1 wherein said plurality of electrodes comprises a pair of transmitting electrodes (2), a pair of receiving electrodes (2'), one of the transmitting and receiving electrodes forming a first pair of electrodes adapted to be applied to the skin of the subject in an upper portion of the manubrium sterni of the subject and a second one of the transmitting and receiving electrodes forming a second pair adapted to be attached to the skin of the patient adjacent the xiphoid process.

9. An apparatus according to claim 8 including a portable elongated housing, a graduated slide, slidably mounted to the housing for extending by different amounts from the housing, the first pair of electrodes containing one transmitting and one receiving electrode being mounted to an outer surface of the housing and the second pair of electrodes including one transmitting and one receiving electrode being mounted to the slide so that a distance between the two pairs of electrodes can be adjusted.

10. An apparatus according to claim 9 wherein said housing comprises an elongated tube, the apparatus including two additional electrodes (1) for capturing the electrocardiogram signal of the subject and a hook (32) on the tube for attaching the tube to a support, the slide (31) comprising a ruler, telescopically engaged to the housing.

11. A process for measuring and processing physiological signals to determine cardiac and circulatory parameters of a subject having a body with a surface, the process comprising:

applying a plurality of electrodes to the surface of the body, over the surface to delimit a volume in the body;

capturing from the electrodes at least one electrocardiographic signal from the subject and at least one impedance signal representing a variation in impedance of the volume of the body;

shaping the electrocardiographic and impedance signals;

digitizing the shaped signals;

preprocessing the digitized and shaped electrocardiographic and impedance signals in a preprocessing unit having a control and a display;

the digital preprocessing unit being programmed to calculate from the electrocardiographic and impedance signals, a plurality of significant parameter data for each heartbeat of the subject, the significant parameter data comprising heart rate (FC), cardiac output (QC), cardiac work (WC), peripheral resistance (RV), a ratio between a derivative of the electrocardiographic signal and a derivative of the impedance signal (IC), an ejection fraction (FE), mean blood pressure (PAM), systolic blood pressure (PAS) and diastolic blood pressure (PAD);

the process including calculating the significant, parameter data for each heartbeat;

collecting and storing the significant parameters in a central digital processing device;

transferring to the central digital processing device data from the unit, using at least one of a detachable storage memory (10) detachably connected to the unit and to the device for transferring data from the unit to the device, and a transmitting element (11) connected between the unit and the device for directly transferring data from the unit and the device;

the central processing device being programmed for analyzing the significant parameter data over a period of a multiplicity of heart beats, the analysis including comparing significant parameter data currently accumulated with previously accumulated significant parameter data, displaying data and printing data; and analyzing the data in the central digital processing device.

12. A process according to claim 6 wherein the operations of capture, filtering, digitization, processing, display and storage on a detachable medium (10) are performed by means (3, 3', 4, 4', 5, 7 and 9) in a portable housing with a power supply, provided with electrodes (1, 2 and 2') in order to record the signals to be processed and stored.

13. A process according to claim 12 including defining the volume (V) by applying the electrodes (2,2') to delimit a truncated cone, a small base (b) of the cone being located near the neck of the subject and the large base (B) of the cone being located near the waist of the subject, and defining a constant (K) such that:

$$K=H\times(D^2+d^2+D\times d-3250)/60$$

with

H=height of the truncated cone in cm,
D=diameter of the large base in cm,
d=diameter of the small base in cm to conduct the analysis.

14. A process according to claim 12, wherein the volume (V) used for measuring the variation in impedance is defined by a truncated cone located between the neck and the thorax at the scyphoid level, allowing a constant (K) to be defined such that:

$$K=H\times(C^2+C^2+Cc-2250)/60$$

with

H=distance between the two receiving electrodes 2',
C=circumference of the thorax at the scyphoid level,
C=circumference of the neck.

15. A process according to claim 12, including determining, on the basis of the ratio (IC) calculated for each heartbeat, in determining the indexed peripheral resistance (RV) using the following formula:

$$RV=\frac{(RV2-RV1)(IC-IC1)}{IC2-IC1}$$

where (RV1) and (RV2) represent values of (RV), and (IC1) and (IC2) represent values of (IC), all determined manually for two different states of the patient and stored during the initialisation operations.

16. A process according to claim 15, including calculating the mean blood pressure (PAM) is calculated for each heartbeat, by using the following formula:

$$PAM=\frac{RV\times QC}{80\times SC}$$

where (QC) represents the cardiac output, (RV) the indexed peripheral resistance and (SC) the body surface of the patient undergoing the process, the value of cardiac work (WC) then being determined by the formula:

$$WC=\frac{0.0144\times PAM\times QC}{SC}$$

17. A process according to claim 16, including determining the diastolic blood pressure (PAD) is determined, for each heartbeat, by means of a polynominal function such that:

$$PAD=F(X,Y)$$

with $$X=A(RV-B)$$

and $$Y=C\times(WC-D)$$

where A, B, C and D represent constants.

18. A process according to claim 17, including using the polynominal function F (X, Y) which has a formulation of the type:

$$F(X,Y)=G\times(X+Y)-I\times(X+Y)^2-J\times(X\times Y)+K+L,$$

where G, I, J, K and L represent constants.

19. A process according to claim 19, including calculating the ejection fraction (FE) by using the formula:

$$FE=-3.54\times W+60$$

on the basis of the parameters:

$$D=\sqrt{1/2\times A^2+1/2\times B^2-AB}$$

where:

A=(RV−2150)/450 and
B=(WC−4.5)/0.9
with:
W=D if A−B≧0
and
W=−D if A−B<0.

20. A process according to claim 12 including generating a set of curves for each heartbeat, the set of curves comprising a first curve (C1) plotting a signal Io representing a variation in impedance in the volume over time, a second curve (C2) plotting a derivative of the variation in impedance over time (dIo), and a third curve (C3) plotting a derivative of the electrocardiographic signal over time, and using said curves to determine heart rate (SC), cardiac output (QC), cardiac work (WC), mean, systolic and diastolic blood pressures (PAM, PAS, PAD).

21. A process according to claim 20, including calculating, for each heartbeat, a value of the ratio IC=dIo/Io, where (Io) represents a difference between the maximum value (MAXC1) and the minimum value (minC1) of the curve (C1), and (dIo) represents the difference between the maximum value (MAXC2) and the most frequent value of the curve (C2), for each heartbeat.

22. A process according to claim 21 including determining the systolic ejected volume (VES) and the heart output (QC) by the following formulae:

$$VES = K \times IC \times TEV$$

and $$QC = VES \times FC.$$

where (TEV), the ventricular ejection time in s, is given by the formula:

$$TEV = H \times [MINC2 - MAXC1) - (MAXC1 - MAXC2)],$$

with H=1.5±0.15, (MINC2) being the minimum value of the curve (C2) for the heartbeat in question.

23. A process according to claim 21, including plotting digitally, for each heartbeat, a curve (C4) expressing the function dI/dt=F'(I) and constituted by a first ovoid loop (BO) representing the mechanical systole and by a second ovoid loop (bO) representing the diastole, then calculating the ratio between the lengths of the major axes office two loops (BO and bO).

24. A process according to claim 20, including, characterised in that it consists in establishing digitally, for each heartbeat and on the basis of numerical values determined for the curves (C1 and C2), a curve (C5) expressing the function (dI/dt)/I=F"(I), where I represents the successive recorded values of the impedance of a defined volume (V) of the body of the subject during a cardiac cycle, and taking the form of a flattened figure of eight, the longitudinal axis of which is inclined by an angle ($\alpha$) relative to the axis corresponding to the variable (I), then in one of measuring and calculating the time taken to pass from the point (O) of intersection of the curve (C4) to the point (F) located at the distal end of the lower loop of said curve (C4), this time corresponding to the ventricular ejection time (TEV).

* * * * *